US009067847B2

United States Patent
Bashir et al.

(10) Patent No.: US 9,067,847 B2
(45) Date of Patent: Jun. 30, 2015

(54) PROCESS FOR PRODUCING A SYNTHESIS GAS MIXTURE

(71) Applicant: Saudi Basic Industries Corporation, Riyadh (SA)

(72) Inventors: Mubarik Ali Bashir, Riyadh (SA); Ijaz Ahmed, Riyadh (SA)

(73) Assignee: SAUDI BASIC INDUSTRIES CORPORATION, Riyadh (SA)

(*) Notice: Subject to any disclaimer, the term of this patent is extended or adjusted under 35 U.S.C. 154(b) by 0 days.

(21) Appl. No.: 13/922,308

(22) Filed: Jun. 20, 2013

(65) Prior Publication Data

US 2013/0345326 A1    Dec. 26, 2013

(30) Foreign Application Priority Data

Jun. 21, 2012  (EP) ..................................... 12004661

(51) Int. Cl.
C07C 27/00        (2006.01)
C07C 1/04         (2006.01)
(Continued)

(52) U.S. Cl.
CPC . *C07C 1/04* (2013.01); *C07C 27/00* (2013.01); *C01B 3/384* (2013.01); *C10K 1/04* (2013.01);
(Continued)

(58) Field of Classification Search
CPC ............... C01B 2203/0238; C01B 2203/0415; C01B 2203/043; C01B 2203/0435; C01B 2203/0475; C01B 2203/0495; C01B 2203/061; C01B 2203/1235; C01B 2203/1241; C01B 3/384; C07C 1/04; C07C 27/00; C10K 1/005; C10K 1/024; C10K 1/04; C10K 1/32; C10K 3/026

USPC ........................................... 518/704; 252/373
See application file for complete search history.

(56) References Cited

U.S. PATENT DOCUMENTS 3,919,114 A * 11/1975 Reynolds ...................... 252/373
6,328,945 B1 * 12/2001 Hufton et al. ............... 423/418.2
(Continued)

FOREIGN PATENT DOCUMENTS

EP    0737647 A2    10/1996
GB    2168718 A      6/1986
(Continued)

OTHER PUBLICATIONS

Extended European Search Report; European Application No. 12004661.0; Date of Mailing: Dec. 7, 2012; 7 Pages.
(Continued)

Primary Examiner — Karl J Puttlitz
Assistant Examiner — Amy C Bonaparte
(74) Attorney, Agent, or Firm — Cantor Colburn LLP

(57) ABSTRACT

Disclosed herein are processes for producing a synthesis gas mixture and for producing an organic chemical product. The process can comprise: (i) steam reforming a feed gas stream comprising one or more hydrocarbons to produce a reformed synthesis gas mixture comprising $H_2$, CO and $CO_2$; (ii) cooling reformed synthesis gas mixture obtained in (i) and removing $H_2O$ from the reformed gas mixture; (iii) subjecting reformed synthesis gas mixture obtained in (ii) to a reverse water gas shift reaction so as to decrease the $H_2$/CO molar ratio of the reformed synthesis gas mixture; and (iv) removing $CO_2$ from synthesis gas mixture obtained in (iii). A first stream of $CO_2$ is added to the gas mixture in step (i) and a second stream of $CO_2$ is added to the gas mixture in step (iii), and wherein the first and/or second streams comprise recycled $CO_2$ removed in step (iv).

20 Claims, 3 Drawing Sheets

(51) Int. Cl.
*C01B 3/38* (2006.01)
*C10K 1/04* (2006.01)
*C10K 1/00* (2006.01)
*C10K 1/02* (2006.01)
*C10K 1/32* (2006.01)
*C10K 3/02* (2006.01)

(52) U.S. Cl.
CPC . *C01B 2203/0233* (2013.01); *C01B 2203/0238* (2013.01); *C01B 2203/0415* (2013.01); *C01B 2203/043* (2013.01); *C01B 2203/0435* (2013.01); *C01B 2203/0475* (2013.01); *C01B 2203/0495* (2013.01); *C01B 2203/061* (2013.01); *C01B 2203/1235* (2013.01); *C01B 2203/1241* (2013.01); *C10K 1/005* (2013.01); *C10K 1/024* (2013.01); *C10K 1/32* (2013.01); *C10K 3/026* (2013.01)

(56) References Cited

U.S. PATENT DOCUMENTS

2003/0014974 A1* 1/2003 Rojey et al. ............... 60/670
2007/0142482 A1 6/2007 Jung et al.
2007/0244208 A1 10/2007 Shulenberger et al.
2010/0105986 A1 4/2010 Miles et al.
2010/0190874 A1 7/2010 Mamedov et al.

FOREIGN PATENT DOCUMENTS

| WO | 2008122399 A1 | 10/2008 |
| WO | 2010069549 A1 | 6/2010 |
| WO | 2011018233 A1 | 2/2011 |

OTHER PUBLICATIONS

International Search Report for Application No. PCT/IB2013/055080; Date of Mailing: Jan. 3, 2014; 5 pages.

Written Opinion of the International Searching Authority for Application No. PCT/IB2013/055080; Date of Mailing: Jan. 3, 2014; 6 pages.

* cited by examiner

PROCESS FOR PRODUCING A SYNTHESIS GAS MIXTURE

CROSS REFERENCE TO RELATED APPLICATIONS

The present application claims priority to European Application Serial No. 12004661.0, filed Jun. 21, 2012, the contents of which are incorporated herein in their entirety by reference.

The invention is directed to a process for producing a synthesis gas mixture. In addition, the invention relates to a process for producing an organic chemical product.

The efficient commercial production of synthesis gas is gaining significant attention as worldwide interest in synthetic fuels and chemical is increasing. Synthesis gas is a versatile feedstock that can be used in the production of a number of hydrocarbons. Synthesis gas is a gaseous mixture containing hydrogen ($H_2$) and carbon monoxide (CO), which may further contain other gas components like carbon dioxide ($CO_2$), water ($H_2O$), methane ($CH_4$), and nitrogen ($N_2$). Natural gas and (light) hydrocarbons are the predominant starting material for making synthesis gas. Synthesis gas is successfully used as synthetic fuel and also in a number of chemical processes, such as synthesis of methanol or ammonia, Fischer-Tropsch type and other olefin syntheses, hydroformylation (oxo process) or carbonylation reactions, reduction of iron oxides in steel production, etc.

The composition of synthesis gas, and thus its suitability for subsequent use for e.g. methanol production, is characterised mainly by its hydrogen and carbon monoxide content, which may me expressed as the $H_2/CO$ molar ratio.

Synthesis gas can be obtained through various chemical and thermochemical processes from almost any carbon source, such as oil, carbon, biomass, or biodegradable waste. The conventional technology for producing synthesis gas from a methane containing feedstock is the reaction with water (steam) at high temperatures, generally called hydrocarbon steam reforming.

If a feedstock is used in a reforming process that is rich in higher hydrocarbons, like naphtha, the feedstock first needs to be treated in a so-called pre-reforming step, in order to convert the heavy hydrocarbons in the feed into methane, hydrogen and carbon oxides. Such higher hydrocarbons are more reactive than methane in steam reforming, and could—if present in the feed—lead to carbon formation and thus to deactivation of the catalyst employed in steam reforming. In such a pre-reformer several reactions take place simultaneously; the most important being hydrocarbon steam reforming (1), water gas shift (2), and methanation (3a, 3b) reactions, which can be represented, respectively as:

$$C_nH_m + nH_2O \leftrightarrow nCO + \left(\frac{m}{2} + n\right)H_2 \tag{1}$$

$$CO + H_2O \leftrightarrow H_2 + CO_2 \tag{2}$$

$$CO + 3H_2 \leftrightarrow CH_4 + H_2O \tag{3a}$$

$$CO_2 + 4H_2 \leftrightarrow CH_4 + 2H_2O \tag{3b}$$

In a steam methane reformer, methane-rich gas is converted into a mixture containing carbon monoxide, carbon dioxide, hydrogen and non-reacted methane and water in the so-called steam reforming (4) and carbon dioxide reforming (5) reactions. These can be represented as follows. Steam reforming involves the endothermic conversion of methane and steam into hydrogen and carbon monoxide according to equation (1).

$$CH_4 + H_2O \leftrightarrow CO + 3H_2 \tag{4}$$

$$CH_4 + CO_2 \leftrightarrow 2CO + 2H_2 \tag{5}$$

It typically occurs at temperatures between 700 and 850° C., pressures between 3 and 25 bar and over Ni-based catalysts.

Steam reforming results in synthesis gas having a $H_2/CO$ molar ratio that is higher than the ratio needed for the synthesis of by-products, such as methanol or derivatives from the Fischer-Tropsch reaction. Industrially, the $H_2/CO$ molar ratio is therefore typically adjusted. The $H_2/CO$ molar ratio can, for instance, be lowered by performing the reverse water gas shift reaction shown in equation (6) in a reverse water gas shift reaction unit.

$$CO_2 + H_2 \rightarrow CO + H_2O \tag{6}$$

Despite being a well-established process, conventional steam reforming presents several drawbacks. An elevated heat supply is necessary in order to achieve a high methane conversion. The heat supply normally comes from combustion of part of the incoming natural gas feedstock or from burning waste gases, such as purge gas. Therefore, a large quantity of $CO_2$, typically ranging from about 0.35 to 0.42 cubic meter ($m^3$) of $CO_2$ per $m^3$ of hydrogen gas produced, is emitted due to both the reaction and the heat requirement. Moreover, an excess of steam must be introduced, approximately at a $H_2O/CH_4$ molar ratio of 3 to 4, in order to avoid the deactivation of the metal catalysts due to carbonaceous deposits, and consequently, operation costs and energy consumption increase. It is for these reasons that alternative processes to steam reforming are being investigated.

A known alternative is the $CO_2$ reforming of methane, or dry reforming, shown in equation (5). This is an endothermic reaction, like steam reforming, but it yields a synthesis gas with a lower $H_2/CO$ molar ratio, i.e. 1:1 in case of complete conversion. Such a reduced $H_2/CO$ molar ratio is preferable, e.g. for the synthesis of higher hydrocarbons via Fischer-Tropsch and adequate for the production of oxygenated derivatives, which eliminates the need to adjust the $H_2/CO$ molar ratio by means of the water gas shift reaction.

Dry reforming of methane constitutes a promising option for the conversion of natural gas into synthesis gas mainly due to the environmental benefits that it offers. The dry reforming reaction turns two greenhouse gases ($CH_4$ and mainly $CO_2$) into a valuable feedstock and may lead to the reduction of $CO_2$ emissions.

However, despite the advantages afforded by the dry reforming of methane, few industrial processes utilise this reaction. The main obstacle to the industrial implementation of $CO_2$ reforming of $CH_4$ is that there are no commercial catalysts that can operate without undergoing deactivation due to carbon deposition. Therefore, many research efforts have been focused on developing suitable catalysts with good lifetime stability.

Furthermore, some efforts have been made to design combinations of dry reforming with steam reforming so as to utilise emitted $CO_2$ for lowering the $H_2/CO$ molar ratio of the synthesis gas produced by the conventional steam reforming.

For example, by recycling the $CO_2$ removed from the reformed synthesis gas mixture to the steam reforming step it is possible to reduce the $H_2/CO$ molar ratio from a value of 5 to a value of 3. Unfortunately, most synthesis processes require a $H_2/CO$ molar ratio of about 2 or less. Accordingly, there is still an excess of $H_2$ in the thus obtained synthesis gas.

This excess of $H_2$ typically has to be separated, for example in a pressure swing absorption unit. The separated $H_2$ will then be burnt, either in the steam reforming step or elsewhere in the plant.

GB-A-2 168 718 discloses a process for the production of synthesis gas wherein a stream of carbon dioxide is added to the high temperature gas leaving the primary steam reforming process unit, after which the resultant mixture is passed over a reverse water gas shift reaction unit so as to convert the carbon dioxide into additional carbon monoxide. The added carbon dioxide may have various sources. It may be carbon dioxide that is removed from the effluent of the water gas phase shift reaction unit or from the natural gas feed, but it may also be imported from an external source.

Although the process of GB-A-2 168 718 has a number of advantages (such as the use of the high temperature of the steam reforming effluent in the endothermic reverse water gas shift reaction) the inventors realised that there is room for improvement, in particular with respect to the conversion efficiency of $CO_2$ to CO in the reverse water gas shift reaction.

Figure 1:
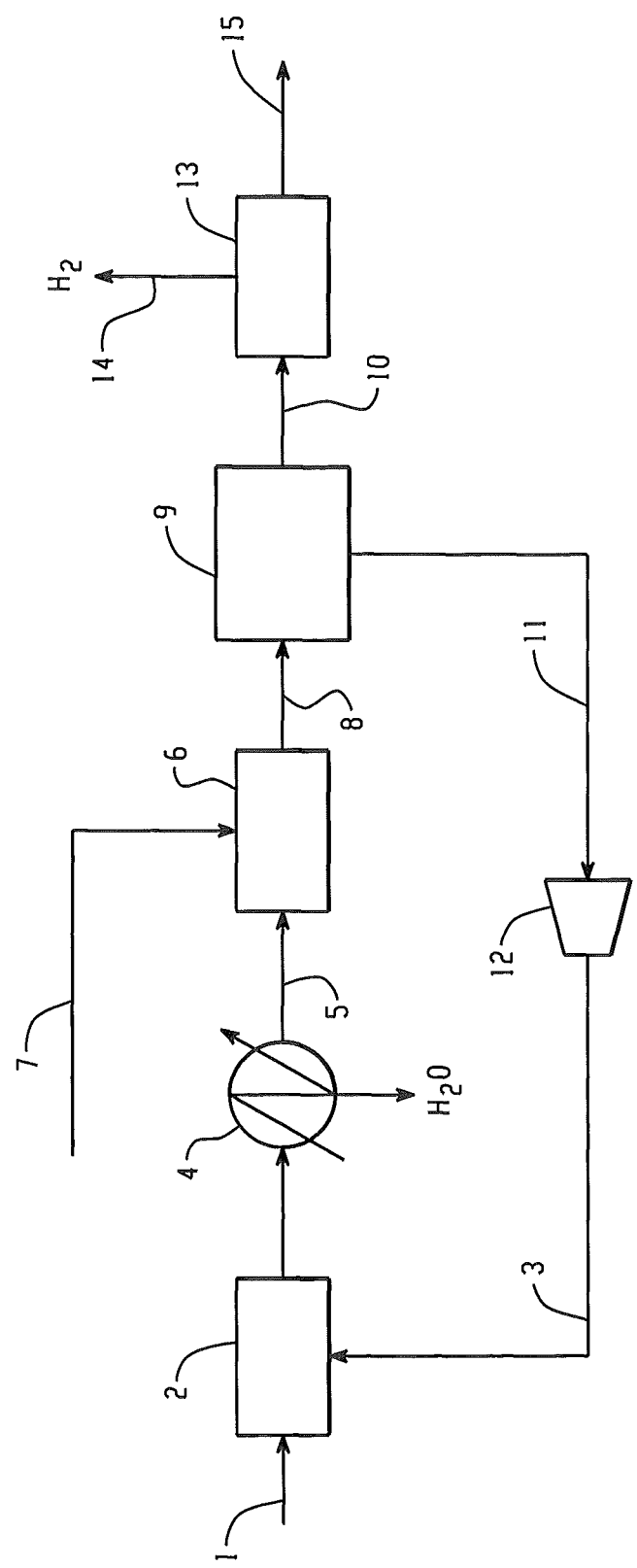
FIG. 1 is a schematic representation of an embodiment of a process for forming synthesis gas.

An objective of the invention is to provide a process for producing a synthesis gas mixture, which is improved over the prior art in particular with respect to conversion of $CO_2$ to CO.

A further objective of the invention is to provide a process for producing a synthesis gas mixture, which can be operated in a relatively small reactor.

Yet a further objective of the invention is to provide a process for producing a synthesis gas mixture, which process results in minimal $CO_2$ emission.

Yet a further objective of the invention is to provide a process for producing a synthesis gas mixture, which synthesis gas mixture has a relatively high $H_2$/CO molar ratio, such as a ratio of 2.5 or less.

The inventors surprisingly found that one or more of these objectives can, at least in part, be met by providing a $CO_2$ recycle from the reverse water gas shift reaction effluent to the steam reformer and adding supplemental $CO_2$ to the reverse water gas shift reaction unit.

Accordingly, in a first aspect the invention is directed to a process for producing a synthesis gas mixture, comprising
 (i) steam reforming a feed gas stream comprising one or more hydrocarbons to produce a reformed synthesis gas mixture comprising $H_2$, CO and $CO_2$;
 (ii) cooling reformed synthesis gas mixture obtained in (i) and removing $H_2O$ from the reformed gas mixture;
 (iii) subjecting reformed synthesis gas mixture obtained in (ii) to a reverse water gas shift reaction so as to decrease the $H_2$/CO molar ratio of the reformed synthesis gas mixture; and
 (iv) removing $CO_2$ from synthesis gas mixture obtained in (iii),
wherein a first stream of $CO_2$ is added to the gas mixture in steam reforming step (i) and a second stream of $CO_2$ is added to the gas mixture in reverse water gas shift reaction step (iii), and wherein at least one of the first and second streams comprises recycled $CO_2$ removed in step (iv).

In accordance with the invention, steam that is contained in the effluent from the steam reforming step (i) is removed from the gas mixture in cooling step (ii). This is highly advantageous because the inventors realised that the presence of steam in the reverse water gas shift reaction limits the conversion efficiency of $CO_2$ to CO. Furthermore, the $H_2$/CO molar ratio of the formed synthesis gas is advantageously low, which allows the resulting synthesis gas to be used for many synthetic applications.

The term "steam reforming" as used in this application (sometimes referred to as steam methane reforming) is meant to refer to a chemical synthesis process, wherein a hydrocarbon containing gas is converted into a mixture comprising hydrogen, carbon monoxide, and carbon dioxide, i.e. synthesis gas. The synthesis gas can further comprise carbon dioxide. Steam reforming usually uses an external source of hot gas to heat tubes in which a catalytic reaction takes place that converts steam and typically small chain hydrocarbons (such as methane) or refinery feedstock into synthesis gas.

The term "reverse water gas shift reaction" as used in this application is meant to refer to a reaction as depicted in equation (6), according to which $CO_2$ is converted in the presence of hydrogen into $H_2O$ and CO.

In a preferred embodiment, the first stream of $CO_2$ comprises $CO_2$ that is removed in step (iv), and the second stream of $CO_2$ originates from an external source. Although not essential, it is preferred that the first stream of $CO_2$ comprises essentially all of the $CO_2$ that is removed in step (iv). The external source for $CO_2$ may be, for instance, an ammonia or fermentation plant, a carbon dioxide well, or carbon dioxide that is recovered from flue gas, or the like. However, it is also possible that this is $CO_2$ which is removed from the feed gas stream prior to the process of the invention.

Alternatively, the first stream of $CO_2$ can originate from an external source, while the second stream of $CO_2$ comprises $CO_2$ that is removed in step (iv). This alternative is, however, less preferred because the amount of $CO_2$ recycle be higher, while the $CO_2$ to CO conversion efficiency in the reverse water gas shift reaction will be lower.

The feed gas stream used in the process of the invention comprises one or more hydrocarbons. As well-known by the person skilled in the art, the term "hydrocarbons" refers to compounds consisting of hydrogen atoms and carbon atoms. Preferably, in accordance with the invention, the feed gas stream comprises hydrocarbons having 1-10 carbon atoms, more preferably 1-6 carbon atoms, and even more preferably 1-3 carbon atoms, such as methane, ethane and/or propane. Preferably, the one or more hydrocarbons that are comprised in the feed gas stream at least comprise methane. In a highly preferred embodiment of the invention, the feed gas stream comprises natural gas.

Steam reforming step (i) can suitably be operated in the presence of one or more catalysts. Normally, the catalyst will be a metal-based catalyst, such as a nickel based catalyst. Preferably, the steam reforming is performed in the presence of one or more catalysts selected from the group consisting of nickel-based catalysts, ruthenium-based catalysts, rhodium-based catalysts, palladium-based catalysts, iridium-based catalysts, and platinum-based catalysts. In view of its low cost, nickel-based catalysts are preferred.

The operation temperature for steam reforming step (i) can suitably be in the range of 700-1000° C., preferably in the range of 800-950° C., more preferably in the range of 850-900° C.

The additional first stream of $CO_2$ which is added to the gas mixture in steam reforming step (i) promotes the conversion to CO and accordingly contributes to a lowering of the $H_2$/CO molar ratio. The addition of the first stream of $CO_2$ may occur before and/or during the reverse water gas shift reaction.

The synthesis gas mixture resulting from steam reforming step (i) is cooled. This can advantageously be done while recovering waste heat. The synthesis gas may suitably be cooled in step (ii) to a temperature in the range of 30-50° C., preferably in the range of 30-40° C. Such temperatures allow the condensing of steam. The condensed water can then conveniently be separated, for example by draining. Accordingly, $H_2O$ is removed from the synthesis gas mixtures obtained in step (i).

The resulting synthesis gas mixture (which is dried, i.e. water has been removed from the gas mixture) is thereafter subjected to a reverse water gas shift reaction together with the second stream of $CO_2$ which is added to this reverse water gas shift reaction step (iii). The addition of the second stream of $CO_2$ may occur before and/or during the reverse water gas shift reaction.

By adding $CO_2$ to the reverse water gas shift reaction step at least some of the $CO_2$ is caused to react with hydrogen to form additional CO. By adding additional $CO_2$ in the reverse water gas shift reaction the CO flow rate is advantageously increased. In addition, the $H_2$/CO molar ratio of the resulting synthesis gas is further reduced.

Reverse water gas shift reaction step (iii) can suitably be operated in the presence of one or more catalysts. Preferably, the reverse water gas shift reaction is performed in the presence of one or more catalysts selected from the group consisting of ZnO, $MnO_x$, alkaline earth metal oxides composite (or mixed metal) oxides (such as those as listed in US-A-2007/0 142 482). Further catalysts are disclosed in US-A-2010/0 105 962, WO-A-2010/069549, and US-A-2010/0 190 874, each of which is herewith completely incorporated by reference.

In a suitable embodiment the reverse water gas shift reaction is performed in an adiabatic reactor. This is a simple type of reactor and therefore desirably in view of costs. Normally, the adiabatic reactor is a cylindrical vessel filled with an appropriate catalyst, wherein reactor feed enters from the top and reactor effluent leaves from the bottom. The reactor is typically rendered adiabatic by being insulated from the outside surface.

In an alternative embodiment, the reverse water gas shift reaction is performed in a gas heated reactor. This embodiment is preferred, since the conversion in an adiabatic reactor is limited by the reactor feed temperature in view of the endothermic nature of the reverse water gas shift reaction. The use of a gas heated reactor overcomes this temperature limitation.

When applying an adiabatic reactor, the operation temperature for reverse water gas shift reaction step (iii) can suitably be 700° C. or less, such as in the range of 625-675° C. This means that the synthesis gas mixture preferably has a temperature of less than 700° C., preferably in the range of 625-675° C., upon being subjected to the reverse water gas shift reaction (i.e. upon entering the reverse water gas shift reaction unit). In order to arrive at such a temperature, the reformed gas mixture that has been cooled in step (ii) (and possibly supplemented with the second stream of $CO_2$) can be heated prior to being subjected to the reverse water gas shift reaction. Nevertheless, this operation temperature for the reverse water gas shift reaction in the invention is considerably lower than the temperature reported for the reverse water gas shift reaction in e.g. GB-A-2 168 718. Without wishing to be bound by any theory, the inventors believe that this may be due to the reduced water content of the gas mixture entering the reverse water gas shift reaction unit.

When applying a gas heated reactor, the synthesis gas mixture entering the reactor can have a temperature of less than 650° C., preferably in the range of 350-550° C. Upon leaving the gas heated reactor, the synthesis gas mixture can have a temperature in the range of 650-750° C. Gas heated reactors have, for instance, been disclosed in WO-A-2008/122399 and WO-A-2011/018233, each of which is herewith completely incorporated by reference. In a gas heated reverse water gas shift reactor, the heat required for performing the reverse water gas shift reaction is provided by passing a hot gas through a shell compartment of the reactor. In this manner, the reactor can be used for carrying out a reaction, but at the same time can serve the purpose of heat exchange. The use of such a gas heated reverse water gas shift reactor thus allows operating the method of the invention in an energetically highly favourable manner.

The invention surprisingly allows a relatively high $CO_2$ to CO conversion efficiency, in particular in reverse water gas shift reaction step (iii). Preferably, the volume percentage of converted $CO_2$ in step (iii) is 30% or more, such as in the range of 30-45%, preferably in the range of 35-40%.

After the reverse water gas shift reaction, the invention comprises a step (iv) wherein remaining $CO_2$ is removed from the resulting synthesis gas mixture. This can be done using conventional means, such as by acquiring proprietary process like Benfield, Catacarb, aMDEA, Rectisol, Selexol. In these well-known processes appropriate solvents are used to absorb $CO_2$ from synthesis gas at relatively elevated pressure. The $CO_2$ rich solvent is then regenerated to separate $CO_2$ from solution. This is typically done by applying heat and reducing pressure. Other processes like pressure swing adsorption (PSA) can also be used. In this process $CO_2$ is selectively adsorbed on an appropriate adsorbent at relatively elevated pressure. The adsorbed $CO_2$ is then separated (desorbed) by reducing pressure.

In accordance with the process of the invention $CO_2$ which is removed from the reverse water gas shift reaction effluent is recycled either to the steam reforming step or to the reverse water gas shift reaction step, and preferably to the steam reforming step. The advantage of such a recycle is that non-converted $CO_2$ is removed from the obtained synthesis gas (thereby lowering the effluent $CO_2$ content) and used in the steam reforming step to promote the $CO_2$ to CO conversion efficiency.

The process of the invention may additionally comprise a step wherein the synthesis gas mixture obtained in step (iv) is reduced in $H_2$ content. Well-known means to do so include pressure swing adsorption, membrane based separation or cryogenic based $H_2$ removal.

The synthesis gas mixture obtained by the method of the invention has an advantageously low $H_2$/CO molar ratio. Preferably, the synthesis gas mixture obtained by the process has a $H_2$/CO molar ratio of 3 or less, preferably 2.5 or less, more preferably 2.2 or less, such as in the range of 1.0-2.2.

An exemplary embodiment of the process of the invention is schematically shown in FIG. 1, which shows a feed gas stream 1 entering a steam reforming unit 2, together with first stream of $CO_2$ 3 after which the reformed synthesis gas mixture is subjected to waste heat recovery and cooling while draining water in unit 4. Subsequently, the cooled and dried gas mixture 5 enters reverse water gas shift reaction unit 6, together with second stream of $CO_2$ 7. The obtained $CO_2$ containing synthesis gas mixture 8 is thereafter subjected to $CO_2$ removal unit 9, which produces a synthesis gas mixture 10 depleted of $CO_2$ and a recycle stream of $CO_2$ 11. Recycle stream 11 is directed to a $CO_2$ recycle compressor 12 to yield first stream of $CO_2$ 3. In the exemplary embodiment shown in FIG. 1, synthesis gas mixture 10 is further subjected to a pressure swing adsorption unit 13 to remove excess H$_2$ 14. Finally, a synthesis gas 15 is obtained with desirably low H$_2$/CO molar ratio.

Figure 2:
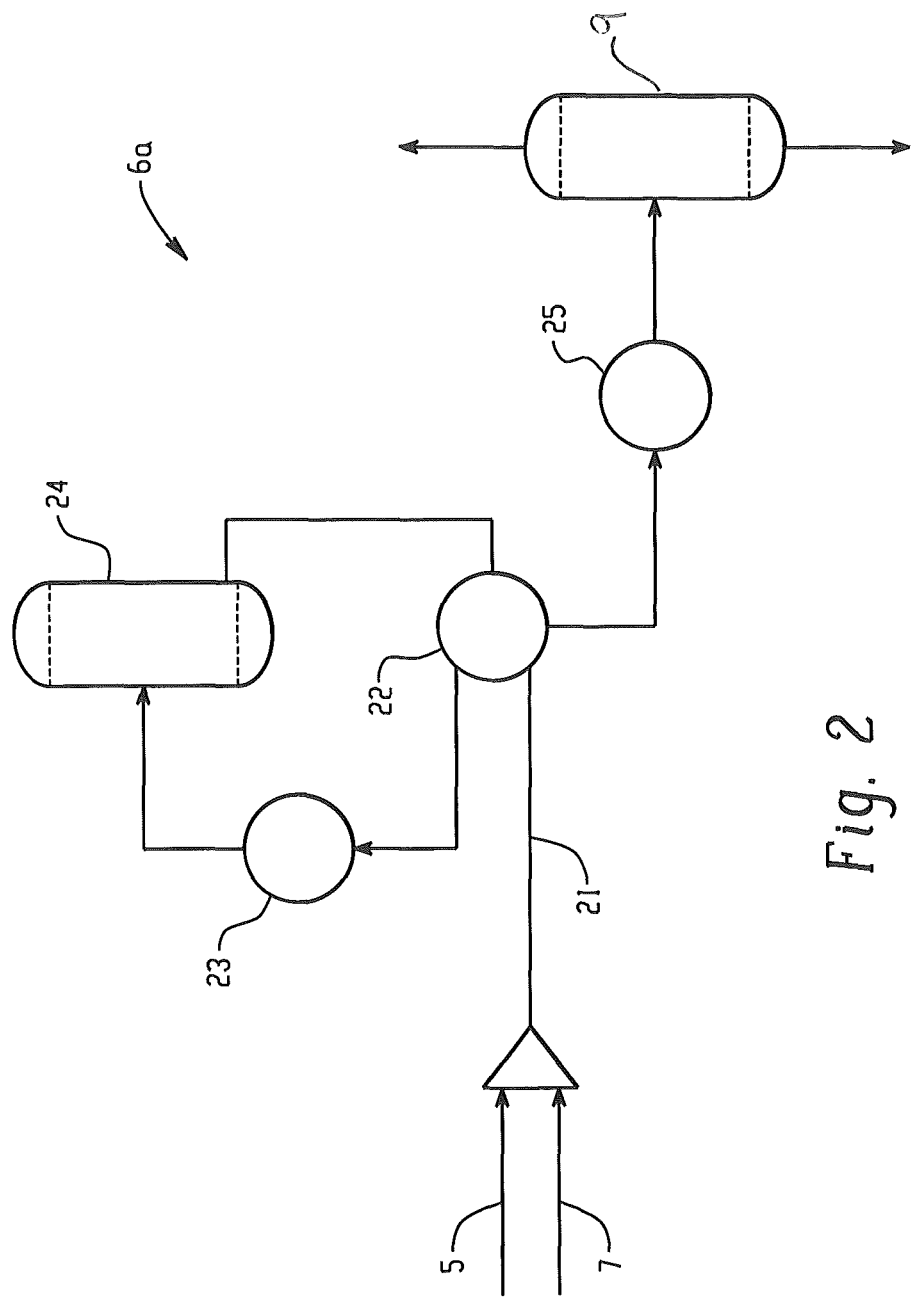
FIG. 2 is a schematic representation of another embodiment of a process for forming synthesis gas using an adiabatic reverse water gas shift unit.

An exemplary embodiment of an adiabatic reverse water gas shift unit 6a is shown in FIG. 2. In this embodiment, cooled and dried gas mixture 5 is combined with second stream of CO$_2$ 7. The combined gas mixture 21 is pre-heated by heat-exchanger 22 and further heated by heater 23 before entering the adiabatic reverse water gas shift reactor 24. Effluent from the adiabatic reverse water gas shift reactor is pre-cooled by heat-exchanger 22 and further cooled by cooler 25 before passing on to CO$_2$ removal unit 9.

Figure 3:
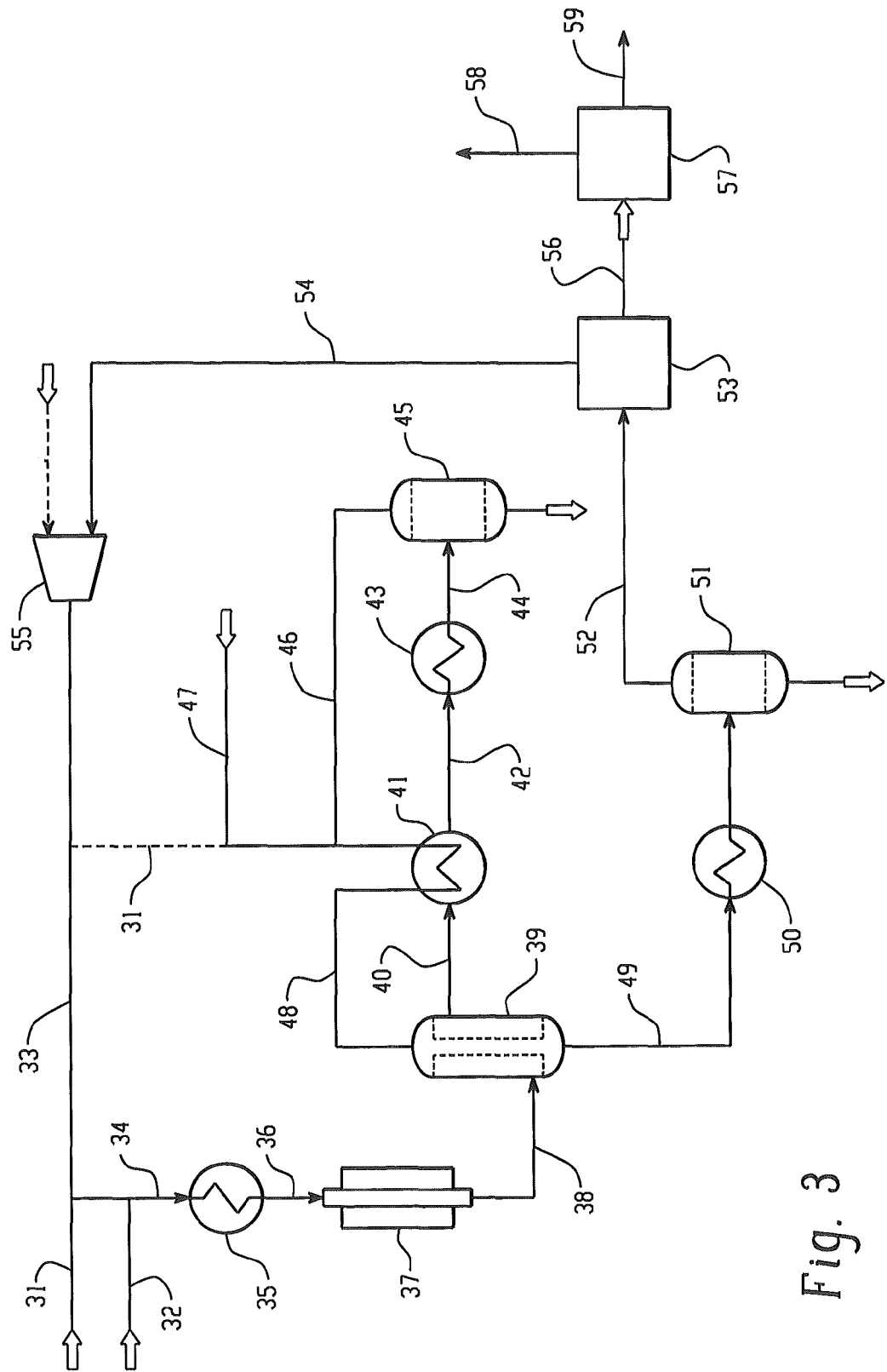
FIG. 3 is a schematic representation of another embodiment of a process for forming synthesis gas.

FIG. 3 shows an alternative exemplary embodiment of the invention, wherein a gas heated reverse water gas shift unit is employed. Feed gas stream 31 (such as a desulfurised natural gas stream), recycle CO$_2$ stream 33 (first stream of CO$_2$) and steam stream 32 are mixed in to stream 34. This stream 34 is preheated in preheater 35. Preheated stream 36 at a temperature of about 450-550° C. enters steam methane reformer 37. Reformed gas stream 38 leaves steam methane reformer 37 at a temperature of about 850-950° C. Hot reformed gas stream 38 is cooled down in a shell compartment of gas heated reverse water gas shift reactor 39 and leaves the shell compartment of this reactor as stream 40 at a temperature of about 600-650° C. Stream 40 is further cooled in gas heated reverse water gas shift reactor feed pre-heater 41 and leaves as stream 42 at a temperature of about 225-275° C. Stream 42 is further cooled in heat exchanger 43 to a temperature of about 25-45° C. while recovering heat and leaves as stream 44. Stream 44 enters knock out drum 45 where the condensed steam in the reformed gas leaves at the bottom and dry reformed gas stream 46 leaves at the top. Dry reformed gas stream 46 is mixed with CO$_2$ stream 47 (second CO$_2$ stream) from an external source and is pre-heated in gas heated reverse water gas shift reactor pre-heater 41 and leaves as pre-heated stream 48 at a temperature of about 350-550° C. Pre-heated stream 48 enters a tube compartment of gas heated reverse water gas shift reactor 39. The tubes in gas heated reverse water gas shift reactor 39 are filled with an appropriate reverse water gas shift catalyst. The endothermic reverse water gas shift reaction takes place over the catalyst in the tube compartment of gas heated reverse water gas shift reactor 39. The required heat of reaction is supplied by the hot reformed gas from shell compartment. Alternatively, or additionally, the required heat of reaction can also be supplied from any other heat source like hot reformed gas from auto thermal reformer or partial oxidation. Effluent stream 49 from gas heated reverse water gas shift reactor 39 is cooled to a temperature of about 25-45° C. in heat exchanger 50 by recovering heat. After separating condensate in knock out drum 51, stream 52 is sent to CO$_2$ removal unit 53 for CO$_2$ separation. The separated CO$_2$ stream 54 is compressed in compressor 55 and compressed CO$_2$ stream 33 is recycled into steam reformer 37. CO$_2$ free synthesis gas stream 56 from CO$_2$ removal unit 53 is subjected to H$_2$ removal unit 57 for H$_2$ to CO molar ratio adjustment. Stream 59 is synthesis gas with a desired H$_2$ to CO ratio and stream 58 represents excess H$_2$.

The process of the invention is particularly advantageous in combination with making organic chemicals from synthesis gas that require a synthesis gas composition with relatively low H$_2$/CO molar ratio, or even about equimolar amounts, like the direct conversion of synthesis gas into dimethyl ether, or the production of methanol for the hydroformylation of light olefins for oxo alcohol synthesis.

Accordingly, in a further aspect the invention is directed to a process for producing an organic chemical product, comprising producing a synthesis gas mixture according to a process of the invention as an intermediate product and converting the synthesis gas mixture so obtained into the organic chemical product.

The invention will now be further illustrated by means of the following examples, which by no means are intended be limiting on the scope.

EXAMPLE 1

A simulation experiment was conducted wherein a synthesis gas production using the process disclosed in GB-A-2 168 718 was compared to a synthesis gas production using the process of the present invention equipped with an adiabatic reverse water gas shift reaction unit having a configuration as shown in FIG. 2. The simulation was carried out using the standard simulation program Pro-II. The results of this simulation experiment are shown in table 1 below. It can be derived from this table that, for the same production of CO, the conversion in the reverse water gas shift reaction using the process of the invention is 8% higher. Furthermore, the total feed to the reverse water gas shift reaction unit is about 40% less, which allows a much smaller reactor and accordingly saves costs. In addition, the CO$_2$ recycle in accordance with the process of the invention is about 60% less than in the process as disclosed in GB-A-2 168 718. As a result, the CO$_2$ removal unit in accordance with the process of the invention can be relatively small and less expensive.

TABLE 1

RSR integration comparison

| Parameter | Units | GB-A-2 168 718 | Example 1 |
|---|---|---|---|
| NG Feed | kg · mol/h | 1000 | 1000 |
| Steam/carbon molar ratio in SMR | | 3.0:1 | 3.0:1 |
| SMR exit temperature | ° C. | 906 | 887 |
| CH$_4$ slip from SMR | Vol. % dry | 0.5 | 0.5 |
| CO$_2$ recycle to SMR/RSR | kg · mol/h | 1546 | 572 |
| Additional CO$_2$ to RSR | kg · mol/h | 300 | 300 |
| Total feed to RSR | kg · mol/h | 7827 | 4873 |
| H$_2$/CO molar ratio after RSR | | 2.02:1 | 2.03:1 |
| Total CO production | kg · mol/h | 1288 | 1282 |
| CO$_2$ conversion in RSR | % | 28.1 | 36.0 |

RSR: reverse water gas shift reactor
SMR: steam methane reformer

EXAMPLE 2

A simulation experiment similar to that of example 1 was conducted. However, in this example a synthesis gas production using the process disclosed in GB-A-2 168 718 was compared to a synthesis gas production using the process of the present invention equipped with a gas heated reverse water gas shift reaction unit having a configuration as shown in FIG. 3. The results of this simulation experiment are shown in table 2 below. In comparison with the process of GB-A-2 168 718, the CO production has significantly increased for the same amount and type of feed. The CO$_2$ conversion has increased from 28.1 for the process of GB-A-2 168 718 to 49.3% which is about 21.2% increase (conversion efficiency has almost doubled). In addition, the CO$_2$ recycle in accordance with the process of the invention is about 60% less than in the process as disclosed in GB-A-2 168 718. As a result, the CO$_2$ removal unit in accordance with the process of the invention can be relatively small and less expensive.

TABLE 2

RSR integration comparison

| Parameter | Units | GB-A-2 168 718 | Example 2 |
|---|---|---|---|
| NG Feed | kg · mol/h | 1000 | 1000 |
| Steam/carbon molar ratio in SMR | | 3.0:1 | 3.0:1 |
| SMR exit temperature | ° C. | 906 | 888 |
| $CH_4$ slip from SMR | Vol. % dry | 0.5 | 0.5 |
| $CO_2$ recycle to SMR/GHRSR | kg · mol/h | 1546 | 587 |
| Additional $CO_2$ to GHRSR | kg · mol/h | 300 | 574 |
| Total feed to GHRSR | kg · mol/h | 7827 | 5166 |
| $H_2$/CO molar ratio after GHRSR | | 2.02:1 | 1.50:1 |
| Total CO production | kg · mol/h | 1288 | 1552 |
| $CO_2$ conversion in GHRSR | % | 28.1 | 49.3 |

GHRSR: gas heated reverse water gas shift reactor
SMR: steam methane reformer

Set forth below are some embodiments of the processes disclosed herein.

EMBODIMENT 1

A process for producing a synthesis gas mixture, comprising: (i) steam reforming a feed gas stream comprising one or more hydrocarbons to produce a reformed gas mixture comprising $H_2$, CO and $CO_2$; (ii) cooling the reformed gas mixture obtained in step (i) and removing $H_2O$ from the reformed gas mixture to produce a second gas mixture; (iii) subjecting the second gas mixture from step (ii) to a reverse water gas shift reaction so as to reduce a $H_2$/CO molar ratio of the second gas mixture to produce a third gas mixture; and (iv) removing $CO_2$ from the third gas mixture obtained in step (iii) to form the synthesis gas mixture and a recycle $CO_2$; wherein a first stream of $CO_2$ is added to the reformed gas mixture in step (i) and a second stream of $CO_2$ is added to the second gas mixture in step (iii); and wherein at least one of the first stream and the second stream comprises the recycle $CO_2$ removed in step (iv).

EMBODIMENT 2

A process for producing a synthesis gas mixture, comprising: (i) steam reforming a feed gas stream comprising one or more hydrocarbons to produce a reformed gas mixture comprising $H_2$, CO and $CO_2$; (ii) cooling the reformed gas mixture obtained in step (i) and removing $H_2O$ from the reformed gas mixture to produce a second gas mixture; (iii) subjecting the second gas mixture from step (ii) to a reverse water gas shift reaction so as to reduce a $H_2$/CO molar ratio of the second gas mixture to produce a third gas mixture; and (iv) removing $CO_2$ from the third gas mixture obtained in step (iii) to form the synthesis gas mixture and a recycle $CO_2$; wherein a first stream of $CO_2$ is added in step (i) and a second stream of $CO_2$ is added in step (iii); and wherein at least one of the first stream and the second stream comprises the recycle $CO_2$ removed in step (iv).

EMBODIMENT 3

A process for producing a synthesis gas mixture, comprising: (i) steam reforming in a steam reformer a feed gas stream comprising one or more hydrocarbons to produce a reformed gas mixture comprising $H_2$, CO and $CO_2$; (ii) cooling the reformed gas mixture obtained in step (i) and removing $H_2O$ from the reformed gas mixture to produce a second gas mixture; (iii) subjecting the second gas mixture from step (ii) to a reverse water gas shift reaction in a reverse water gas shift reactor so as to reduce a $H_2$/CO molar ratio of the second gas mixture to produce a third gas mixture; and (iv) removing $CO_2$ from the third gas mixture obtained in step (iii) to form a synthesis gas mixture and a recycle $CO_2$; wherein a first stream of $CO_2$ is added to the steam reformer in step (i) and a second stream of $CO_2$ is added to the reverse water gas shift reactor in step (iii); and wherein at least one of the first stream and the second stream comprises the recycle $CO_2$ removed in step (iv).

EMBODIMENT 4

The process according to any one of Embodiments 1-3, wherein the first stream of $CO_2$ comprises the recycle $CO_2$ removed in step (iv), and wherein the second stream of $CO_2$ originates from an external source.

EMBODIMENT 5

The process according to any one of Embodiments 1-4, wherein step (i) is performed in the presence of a catalyst.

EMBODIMENT 6

The process according to Embodiment 5, wherein the first catalyst comprises at least one of the following nickel-based catalyst, ruthenium-based catalyst, rhodium-based catalyst, palladium-based catalyst, iridium-based catalyst, and platinum-based catalyst.

EMBODIMENT 7

The process according to Embodiment 6, wherein step (i) is performed in the presence of a nickel-based catalyst.

EMBODIMENT 8

The process according to any one of Embodiments 1-7, wherein the reformed gas mixture obtained in step (i) has a first temperature of 700 to 1,000° C.

EMBODIMENT 9

The process according to Embodiment 8, wherein the first temperature is 800 to 950° C.

EMBODIMENT 10

The process according to Embodiment 8, wherein the first temperature is 850 to 900° C.

EMBODIMENT 11

The process according to any one of Embodiments 1-10, wherein the second gas mixture is cooled in step (ii) to a second temperature of 30-50° C.

EMBODIMENT 12

The process according to Embodiment 11, wherein the second temperature is 30-40° C.

EMBODIMENT 13

The process according to any one of Embodiments 1-12, wherein step (iii) is carried out in the presence of a second catalyst.

EMBODIMENT 14

The process according to any one of Embodiments 1-13, wherein the second catalyst comprises at least one of the following ZnO, $MnO_x$, alkaline earth metal oxides composite, and alkaline earth mixed metal oxides composites.

EMBODIMENT 15

The process according to any one of Embodiments 1-14, wherein step (iii) is performed in an adiabatic reactor, and wherein the second gas mixture has a third temperature of less than 700° C. upon being subjected to the reverse water gas shift reaction.

EMBODIMENT 16

The process according to Embodiment 15, wherein the third temperature is 625-675° C.

EMBODIMENT 17

The process according to any one of Embodiments 1-14, wherein step (iii) is performed in a gas heated reactor, and wherein the second gas mixture has a third temperature of less than 650° C. upon being subjected to the reverse water gas shift reaction.

EMBODIMENT 18

The process according to any one of Embodiments 15-17, wherein the third temperature is 350-550° C.

EMBODIMENT 19

The process according to any of Embodiments 17-18, wherein the gas heated reactor comprises a shell compartment for passing hot gas and a tube compartment for carrying out the reverse water gas shift reaction.

EMBODIMENT 20

The process according to any one of Embodiments 1-19, wherein the volume percentage of converted $CO_2$ in step (iii) is 30% or more.

EMBODIMENT 21

The process according to Embodiment 20, wherein the volume percentage of converted $CO_2$ is 30-45%.

EMBODIMENT 22

The process according to Embodiment 21, wherein the volume percentage of converted $CO_2$ is 35-40%.

EMBODIMENT 23

The process according to any one of Embodiments 1-22, further comprising (v) reducing $H_2$ in the synthesis gas mixture obtained in step (iv).

EMBODIMENT 24

The process according to Embodiment 23, wherein step (v) comprises pressure swing adsorption, membrane based separation, or cryogenic based $H_2$ removal.

EMBODIMENT 25

The process according to any one of Embodiments 1-24, wherein the synthesis gas mixture has a $H_2/CO$ molar ratio of 3 or less.

EMBODIMENT 26

The process according to Embodiment 25, wherein the $H_2/CO$ molar ratio is 2.5 or less.

EMBODIMENT 27

The process according to Embodiment 26, wherein the $H_2/CO$ molar ratio is 2.2 or less.

EMBODIMENT 28

The process according to Embodiment 1 or 2, wherein the hydrocarbon in the feed gas stream comprise $CH_4$.

EMBODIMENT 29

The process according to Embodiment 3, wherein the hydrocarbon in the feed gas stream comprises natural gas.

EMBODIMENT 30

A process for producing an organic chemical product, comprising: producing a synthesis gas mixture according to the process of any one of Embodiments 1-29 as an intermediate product; and converting the synthesis gas mixture into the organic chemical product.

EMBODIMENT 31

The process according to Embodiment 30, wherein the organic chemical product comprises methanol, dimethyl ether, oxo alcohols, olefins, wax, synthetic fuel, and a combination comprising at least one of the foregoing.

What is claimed is:

1. A process for producing a synthesis gas mixture, comprising:
    (i) steam reforming a feed gas stream comprising hydrocarbon to produce a reformed gas mixture comprising $H_2$, CO and $CO_2$;
    (ii) cooling the reformed gas mixture obtained in step (i) and removing $H_2O$ from the reformed gas mixture to produce a second gas mixture;
    (iii) subjecting the second gas mixture from step (ii) to a reverse water gas shift reaction so as to reduce a $H_2/CO$ molar ratio of the second gas mixture to produce a third gas mixture; and
    (iv) removing $CO_2$ from the third gas mixture obtained in step (iii) to form a synthesis gas mixture and a recycle $CO_2$;
    wherein a first stream of $CO_2$ is added in step (i) and a second stream of $CO_2$ is added in step (iii); and
    wherein at least one of the first stream and the second stream comprises the recycle $CO_2$ removed in step (iv); and
    wherein the volume percentage of converted $CO_2$ in step (iii) is 30-45%.

2. The process according to claim 1, wherein the first stream of $CO_2$ comprises the recycle $CO_2$ removed in step (iv), and wherein the second stream of $CO_2$ originates from an external source.

3. The process according to claim 1, wherein step (i) is performed in the presence of a catalyst, and wherein the first catalyst comprises at least one of the following nickel based catalyst, ruthenium based catalyst, rhodium based catalyst, palladium based catalyst, iridium based catalyst, and platinum based catalyst.

4. The process according to claim 3, wherein step (i) is performed in the presence of a nickel based catalyst.

5. The process according to claim 1, wherein the reformed gas mixture obtained in step (i) has a first temperature of 700 to 1,000° C.

6. The process according to claim 1, wherein the second gas mixture is cooled in step (ii) to a second temperature of 30-50° C.

7. The process according to claim 6, wherein the second temperature is 30-40° C.

8. The process according to claim 1, wherein step (iii) is carried out in the presence of a second catalyst, and wherein the second catalyst comprises at least one of the following ZnO, $MnO_x$, alkaline earth metal oxides composite, and alkaline earth mixed metal oxides composites.

9. The process according to claim 1, wherein step (iii) is performed in an adiabatic reactor, and wherein the second gas mixture has a third temperature of less than 700° C. upon being subjected to the reverse water gas shift reaction.

10. The process according to claim 9, wherein the third temperature is 625-675° C.

11. The process according to claim 9, wherein the third temperature is 350-550° C.

12. The process according to claim 1, wherein the volume percentage of converted $CO_2$ is 35-40%.

13. The process according to claim 1, further comprising (v) reducing the amount of $H_2$ in the synthesis gas mixture obtained in step (iv).

14. The process according to claim 13, wherein step (v) comprises pressure swing adsorption, membrane based separation, or cryogenic based $H_2$ removal.

15. The process according to claim 1, wherein the synthesis gas mixture has a $H_2$/CO molar ratio of 3 or less.

16. The process according to claim 1, wherein the $H_2$/CO molar ratio is 2.5 or less.

17. A process for producing an organic chemical product, comprising:
    producing a synthesis gas mixture according to the process of claim 1 as an intermediate product; and
    converting the synthesis gas mixture into the organic chemical product.

18. The process according to claim 17, wherein the organic chemical product comprises methanol, dimethyl ether, oxo alcohols, olefins, wax, synthetic fuel, and a combination comprising at least one of the foregoing.

19. The process according to claim 1, wherein the $H_2$/CO molar ratio is 1.0-2.2.

20. The process according to claim 1, wherein step (iii) is performed in a gas heated reactor, and wherein the second gas mixture entering the gas heated reactor has a third temperature of 350-550° C.

* * * * *